(12) United States Patent
Jansheski

(10) Patent No.: US 7,832,404 B2
(45) Date of Patent: Nov. 16, 2010

(54) LOW PROFILE MOUTHGUARD

(75) Inventor: John M. Jansheski, Maryville, TN (US)

(73) Assignee: DenTek Oral Care, Inc., Maryville, TN (US)

( * ) Notice: Subject to any disclaimer, the term of this patent is extended or adjusted under 35 U.S.C. 154(b) by 0 days.

(21) Appl. No.: 12/133,852

(22) Filed: Jun. 5, 2008

(65) Prior Publication Data

US 2009/0159089 A1    Jun. 25, 2009

Related U.S. Application Data

(63) Continuation-in-part of application No. 29/299,274, filed on Dec. 21, 2007, now Pat. No. Des. 614,304.

(51) Int. Cl.
*A61C 5/14* (2006.01)
*A61C 3/00* (2006.01)

(52) U.S. Cl. .......................... 128/859; 128/861; 433/6; D24/180

(58) Field of Classification Search ............... 128/859, 128/861; 433/6; D24/180
See application file for complete search history.

(56) References Cited

U.S. PATENT DOCUMENTS

| | | | |
|---|---|---|---|
| 2,423,005 A | 6/1947 | Chaiken | |
| 3,532,091 A | 10/1970 | Lerman | |
| 4,676,745 A * | 6/1987 | Zurita | 433/6 |
| 4,881,896 A | 11/1989 | Bergersen | |
| D373,421 S | 9/1996 | Brown | |
| 5,718,575 A | 2/1998 | Cross, III | |
| D397,442 S | 8/1998 | Kittelsen | |
| 5,826,581 A * | 10/1998 | Yoshida | 128/859 |
| 5,836,761 A * | 11/1998 | Belvedere et al. | 433/6 |
| 5,873,365 A | 2/1999 | Brown | |
| D406,405 S | 3/1999 | Yoshida | |
| 5,879,155 A | 3/1999 | Kittelsen | |
| 6,012,919 A | 1/2000 | Cross, III et al. | |
| 6,152,138 A * | 11/2000 | Brown et al. | 128/859 |
| 6,164,278 A | 12/2000 | Nissani | |
| 6,200,133 B1 | 3/2001 | Kittelsen | |
| 6,237,601 B1 | 5/2001 | Kittlesen et al. | |
| 6,371,758 B1 | 4/2002 | Kittelsen | |

(Continued)

*Primary Examiner*—Patricia M Bianco
*Assistant Examiner*—Victoria Hicks
(74) *Attorney, Agent, or Firm*—Proskauer Rose LLP

(57) ABSTRACT

A dental appliance for prevention of Bruxism includes a U-shaped buccal strap having opposing right and left aft end portions. A right bite pad assembly is slidingly connected to and completely encloses the right aft end portion of the buccal strap. A left bite pad assembly is slidingly connected to and completely encloses the left aft end portion of the buccal strap. The right bite pad assembly can include a right upper bite surface member for contacting right upper molars of a wearer and a right lower bite surface member for contacting right lower molars of the wearer. The left bite pad assembly can include a left upper bite surface member for contacting left upper molars of a wearer and a left lower bite surface member for contacting left lower molars of the wearer. A right channel extends through the right upper bite surface member and the right lower bite surface member. A left channel extends through the left upper bite surface member and the left lower bite surface member. The right channel receives the right aft end portion of the buccal strap, and the left channel receives the left aft end portion of the buccal strap.

12 Claims, 14 Drawing Sheets

U.S. PATENT DOCUMENTS

| | | |
|---|---|---|
| 6,415,794 B1 | 7/2002 | Kittelsen et al. |
| 6,539,943 B1 | 4/2003 | Kittelsen et al. |
| 6,626,180 B1 | 9/2003 | Kittelsen et al. |
| 6,691,710 B2 | 2/2004 | Kittelsen et al. |
| 6,830,051 B1 | 12/2004 | Lesniak et al. |
| 6,978,786 B2 | 12/2005 | Sabbagh |
| 7,047,978 B2 * | 5/2006 | Zuk .......................... 128/848 |
| 7,506,651 B2 * | 3/2009 | Anonsen .................... 128/859 |
| 2006/0011204 A1 | 1/2006 | Maher |
| 2006/0096602 A1 | 5/2006 | Brown |

* cited by examiner

Section A-A

Section B-B

Section C-C

Section D-D

Section E-E

LOW PROFILE MOUTHGUARD

This application claims priority as a continuation-in-part of co-pending U.S. design patent application Ser. No. 29/299,274 filed Dec. 21, 2007, titled LOW PROFILE MOUTHGUARD, the entire contents of which are incorporated herein by reference.

FIELD

This invention relates to the field of dental appliances. More particularly, this invention relates to an appliance to be worn at night to prevent Bruxism.

BACKGROUND

Bruxism is clenching and/or grinding of the teeth caused by the activation of a reflex chewing activity. Bruxism can cause chips and cracks in the teeth and wear of the biting surface. Bruxism typically occurs during sleep. In a typical case, the canines and incisors move laterally against each other, thereby causing abrasion of tooth enamel, removal of the sharp biting surfaces and flattening of the edges of the teeth. Sometimes, there is a tendency to grind the molars together, which can be loud enough to wake a sleeping partner. In some cases, clenching occurs without significant lateral jaw movement.

Although dental guards exist for preventing Bruxism, prior guards have not provided a comfortable fit in the wearer's mouth. Due to discomfort associated with prior guards, many Bruxism sufferers have given up on the use of guards to treat the problem during sleep. One problem with prior guards is the lack of adjustability to fit a particular wearer's mouth.

Although some prior guards had adjustable bite pads, those guards included adjustment structures that are bulky and uncomfortable to wear. For example, U.S. Patent Application Publication No. 2006/0096602 describes a mouthguard having bite pads whose front-to-back positions may be adjusted by sliding a pin assembly forward or backward to various receiver holes provided in a buccal strap. This pin assembly includes a bulky shank and cap structure that occupies a considerable amount of space between the wearer's cheek and gum. U.S. Pat. No. 6,152,138 describes adjustable bite pads that include a shank and ball structure. The ball of this structure extends outward from the outside surface of the buccal strap where it is prone to rub against the wearer's cheek. Thus, each of these prior art guards include uncomfortable adjustment mechanisms.

What is needed is a size-adjustable mouthguard for preventing Bruxism that includes a low-profile adjustment mechanism which is comfortable enough to be worn overnight by persons with various sized jaws and mandibles.

SUMMARY

The above and other needs are met by a dental appliance that comprises a U-shaped buccal strap having opposing right and left aft end portions, a right bite pad assembly slidingly connected to and completely enclosing the right aft end portion of the buccal strap, and a left bite pad assembly slidingly connected to and completely enclosing the left aft end portion of the buccal strap. The right bite pad assembly comprises a right upper bite surface member for contacting right upper molars of a wearer and a right lower bite surface member for contacting right lower molars of the wearer. The left bite pad assembly comprises a left upper bite surface member for contacting left upper molars of a wearer and a left lower bite surface member for contacting left lower molars of the wearer. A right channel extends through the right upper bite surface member and the right lower bite surface member. A left channel extends through the left upper bite surface member and the left lower bite surface member. The right channel receives the right aft end portion of the buccal strap, and the left channel receives the left aft end portion of the buccal strap.

In some preferred embodiments, the buccal strap includes a plurality of indentations disposed adjacent the right and left aft end portions. The right bite pad assembly includes a protrusion extending inwardly within the right channel, and the left bite pad assembly includes a protrusion extending inwardly within the left channel. The protrusions in the right and left channels are for engaging one of the plurality of indentations in the right and left aft end portions of the buccal strap, thereby providing a means for adjusting the size of the dental appliance.

In some embodiments, a forward portion of the right channel extends through the right upper bite surface member and a rear portion of the right channel extends through the right lower bite surface member. Similarly, a forward portion of the left channel extends through the left upper bite surface member and a rear portion of the left channel extends through the left lower bite surface member.

In one embodiment, the upper bite surface members are formed of a material having a color which is different from the color of the material of the lower bite surface members. When the material of the upper bite surface members wears through due to extended use of the appliance, the material of the lower bite surface members is exposed, thereby clearly indicating that replacement of the appliance is desirable. In an alternative embodiment, the upper and lower bite surface members are formed of materials having the same color.

Some preferred embodiments include a central arched portion in the buccal strap for accommodating the frenulum of a wearer's lower lip.

A trough or channel may be provided in a buccal corner of each of the right and left upper bite surface members. The trough or channel is operable to allow flexing of the bite pad assemblies to accommodate wearer-to-wearer variations in the Curve of Wilson.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
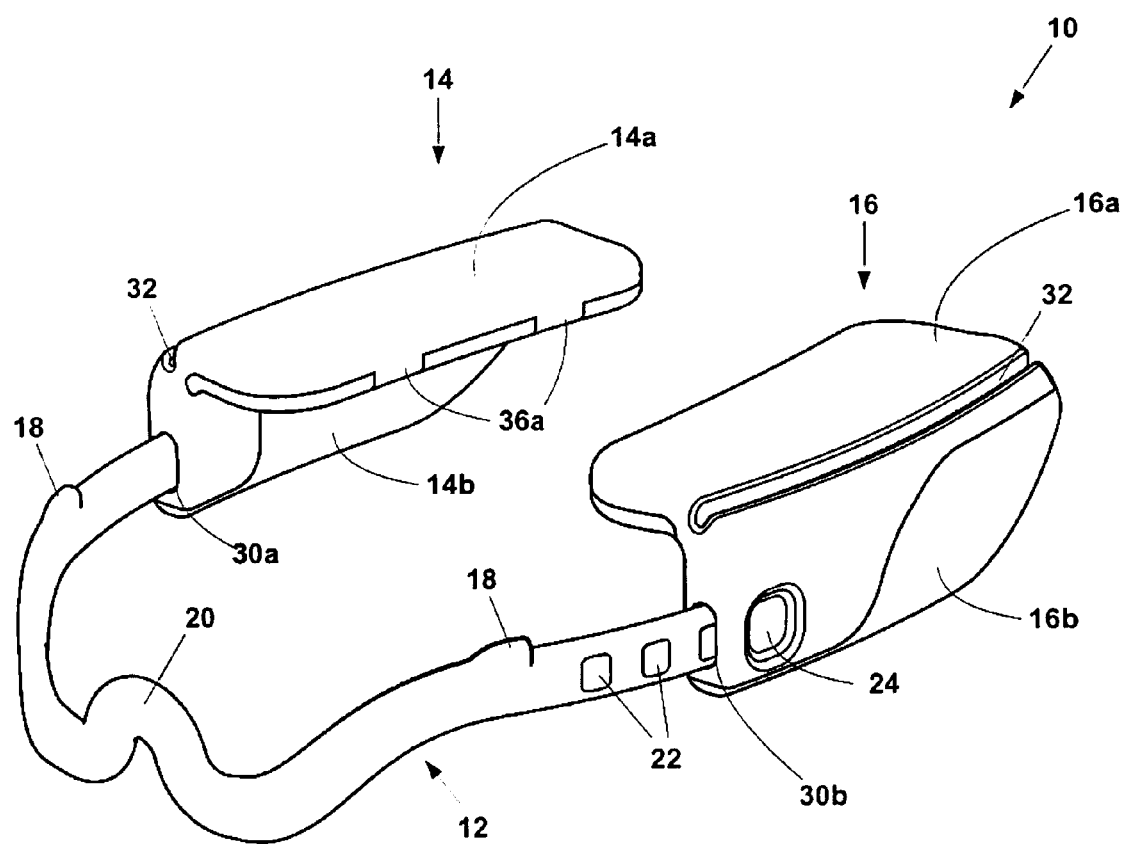
FIG. 1 depicts a front upper perspective view of a low profile mouthguard according to a preferred embodiment of the invention.
Figure 2:
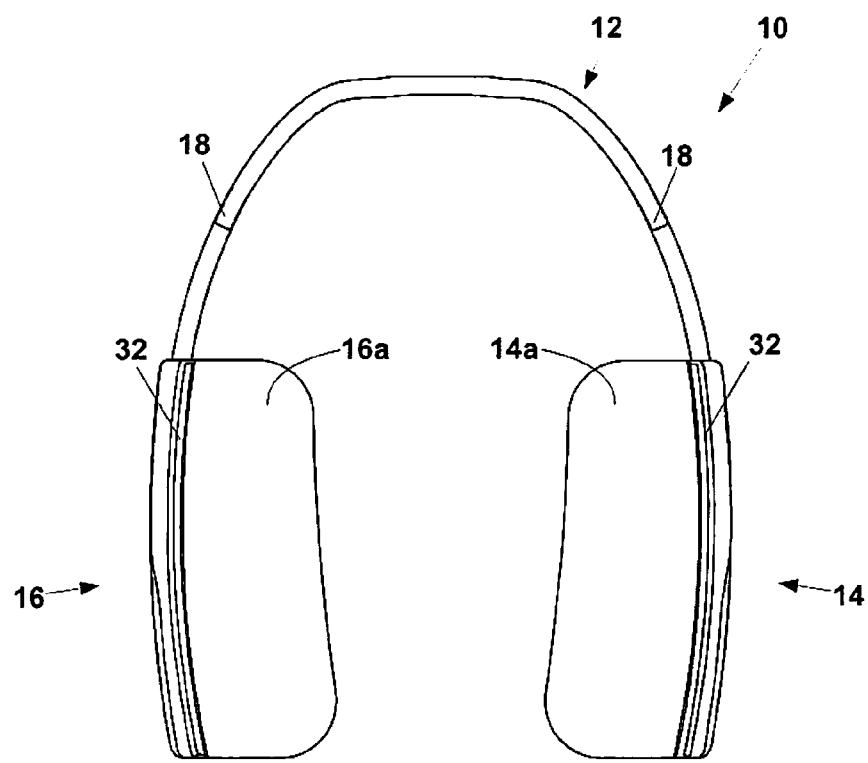
FIG. 2 depicts a top plan view of a low profile mouthguard according to a preferred embodiment of the invention.
Figure 3:
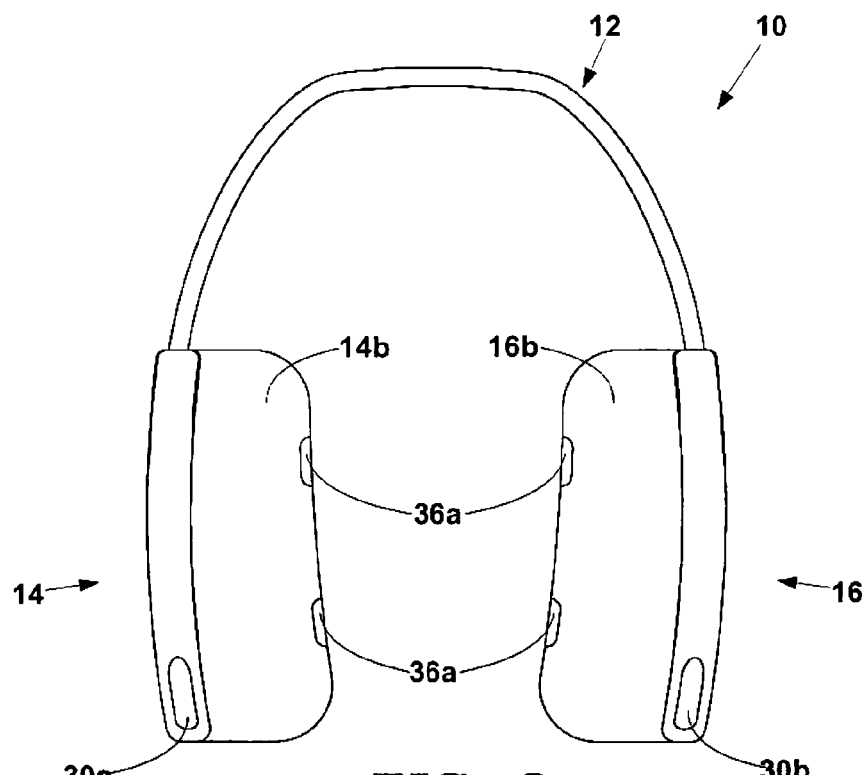
FIG. 3 depicts a bottom plan view of a low profile mouthguard according to a preferred embodiment of the invention.
Figure 4:
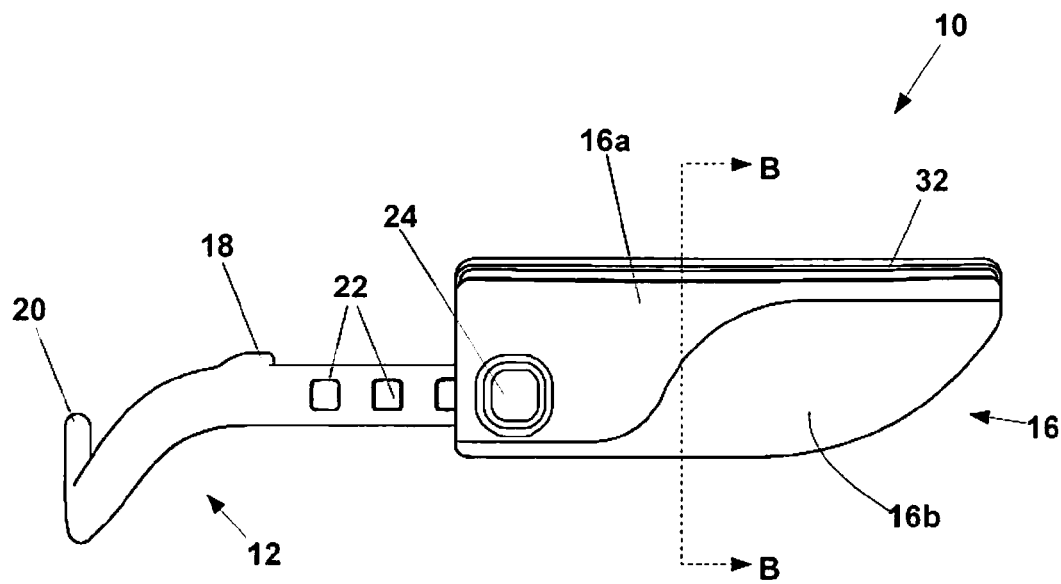
FIG. 4 depicts a left side elevation view of a low profile mouthguard according to a preferred embodiment of the invention.
Figure 5:
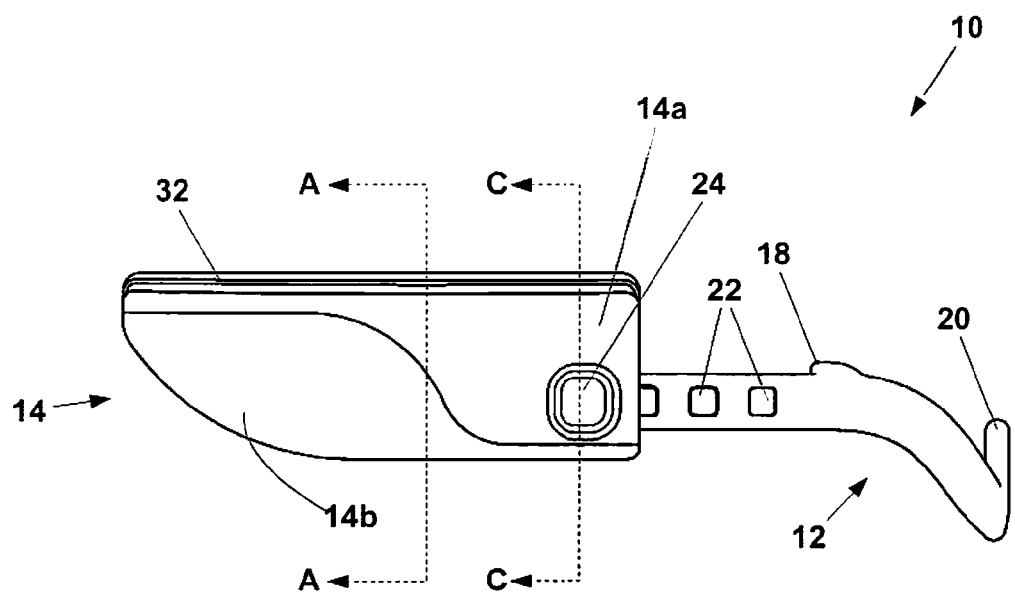
FIG. 5 depicts a right side elevation view of a low profile mouthguard according to a preferred embodiment of the invention.
Figure 6:
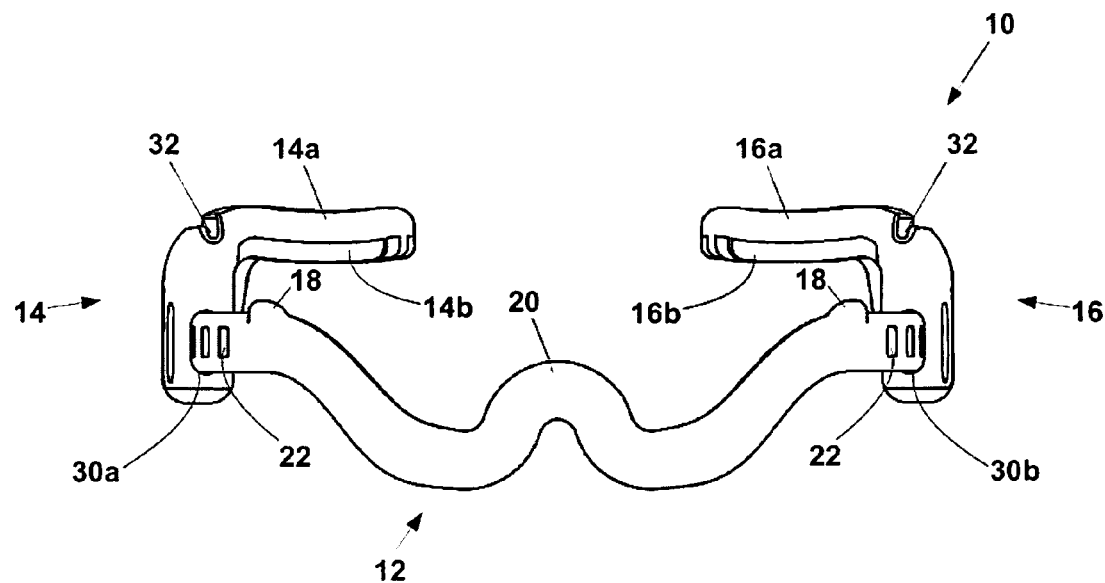
FIG. 6 depicts a front elevation view of a low profile mouthguard according to a preferred embodiment of the invention.
Figure 7:
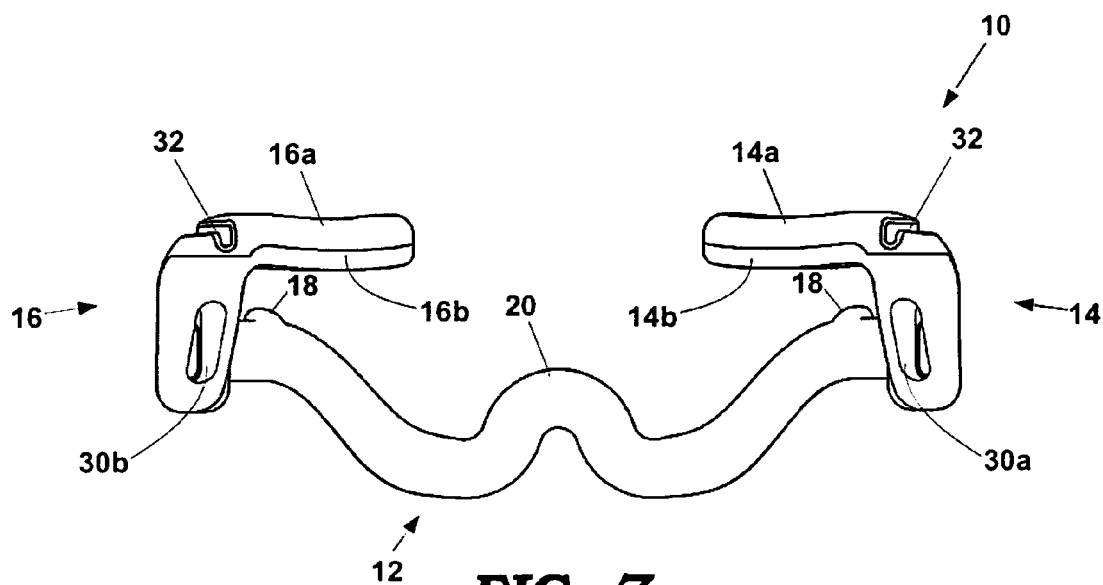
FIG. 7 depicts a rear elevation view of a low profile mouthguard according to a preferred embodiment of the invention.
Figure 8:
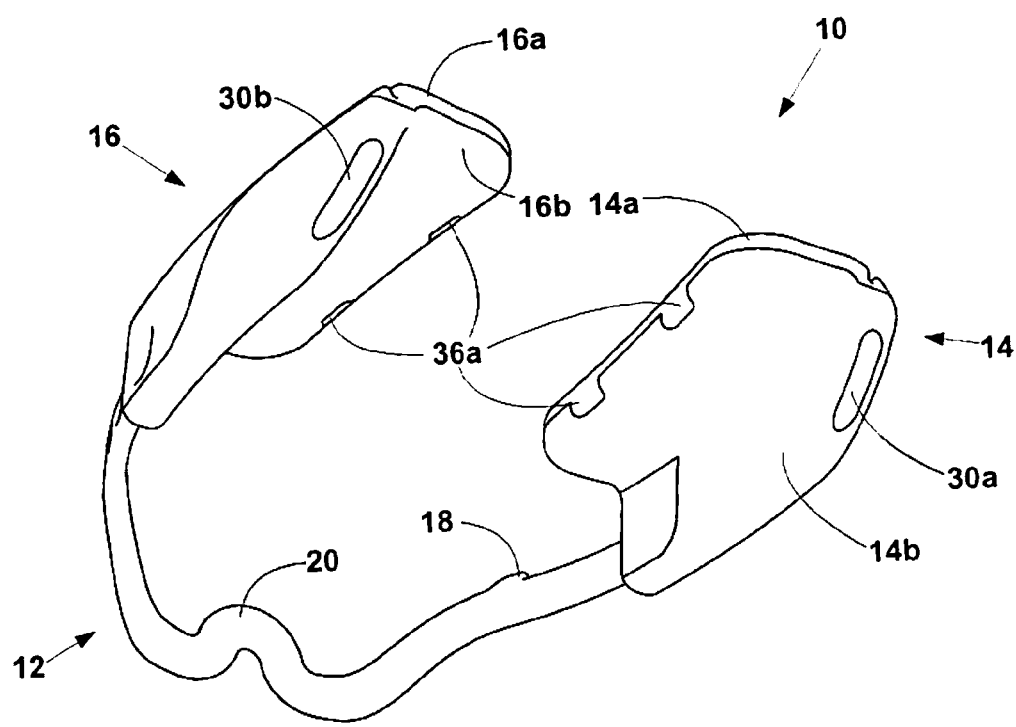
FIG. 8 depicts a rear lower perspective view of a low profile mouthguard according to a preferred embodiment of the invention.
Figure 9:
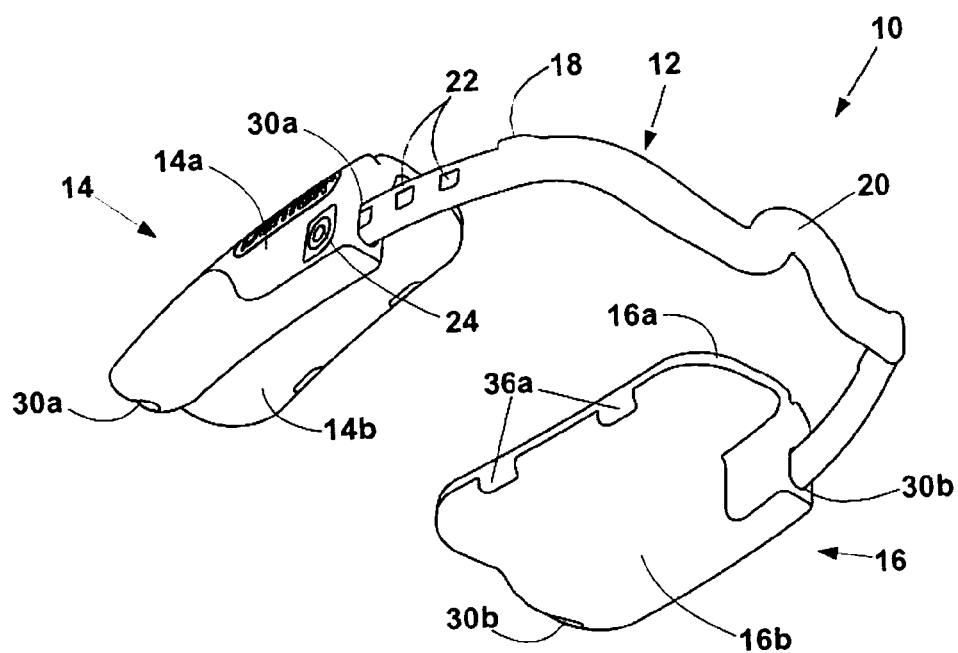
FIG. 9 depicts a front lower perspective view of a low profile mouthguard according to a preferred embodiment of the invention.
Figure 10:
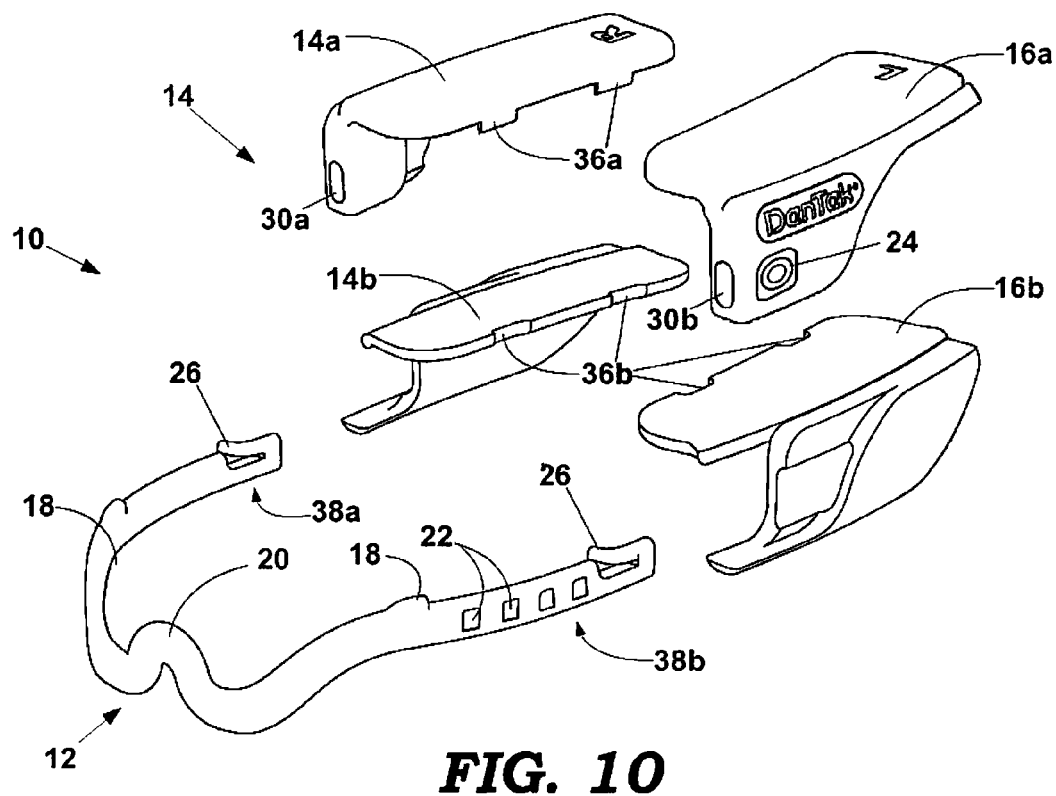
FIG. 10 depicts an exploded view of a low profile mouthguard according to a preferred embodiment of the invention.

As shown in FIG. 1, a preferred embodiment of a dental appliance, which is also referred to herein as a low profile mouthguard 10, includes three main parts: a right bite pad assembly 14, a left bite pad assembly 16 and a buccal strap 12 which connects the two bite pad assemblies 14-16. In the embodiment of FIG. 1, each bite pad assembly 14 and 16 comprises two components: an upper bite surface member 14a-16a and a lower bite surface member 14b-16b. The exploded view of FIG. 10 shows the upper bite surface members 14a-16a separated from the lower bite surface members 14b-16b.

In a preferred embodiment, the upper bite surface members 14a-16a are formed of DuPont Elvax® 550 resin, which is a copolymer of ethylene and vinyl acetate (15% by weight) having a Vicat softening temperature of 62° C. and a Shore A hardness of 92. The lower bite surface members 14b-16b are also preferably formed of the DuPont Elvax® 550 resin. The buccal strap 12 is preferably formed of DuPont Elvax® 750 resin. However, it will be appreciated that the invention is not limited to any particular material or combination of materials for these components.

In preferred embodiments, all of the components of the mouthguard 10 are formed by injection molding. The upper bite surface members 14a-16a may be molded over the lower bite surface members 14b-16b, or they may be formed separately and then assembled with the lower bite surface members 14b-16b.

As shown in the figures, the right and left aft ends 38a-38b of the buccal strap 12 are received within right and left channels 30a-30b that extend down the length of the right and left bite pad assemblies 14-16. The channels 30a-30b are sized to allow the bite pad assemblies 14-16 to move forward and aft relative to the aft ends 38a-38b of the buccal strap 12. In this configuration, the overall length of the mouthguard 10 may be adjusted to fit various mouth sizes by adjusting the forward-aft position of the bite pad assemblies 14-16.

Figure 14:
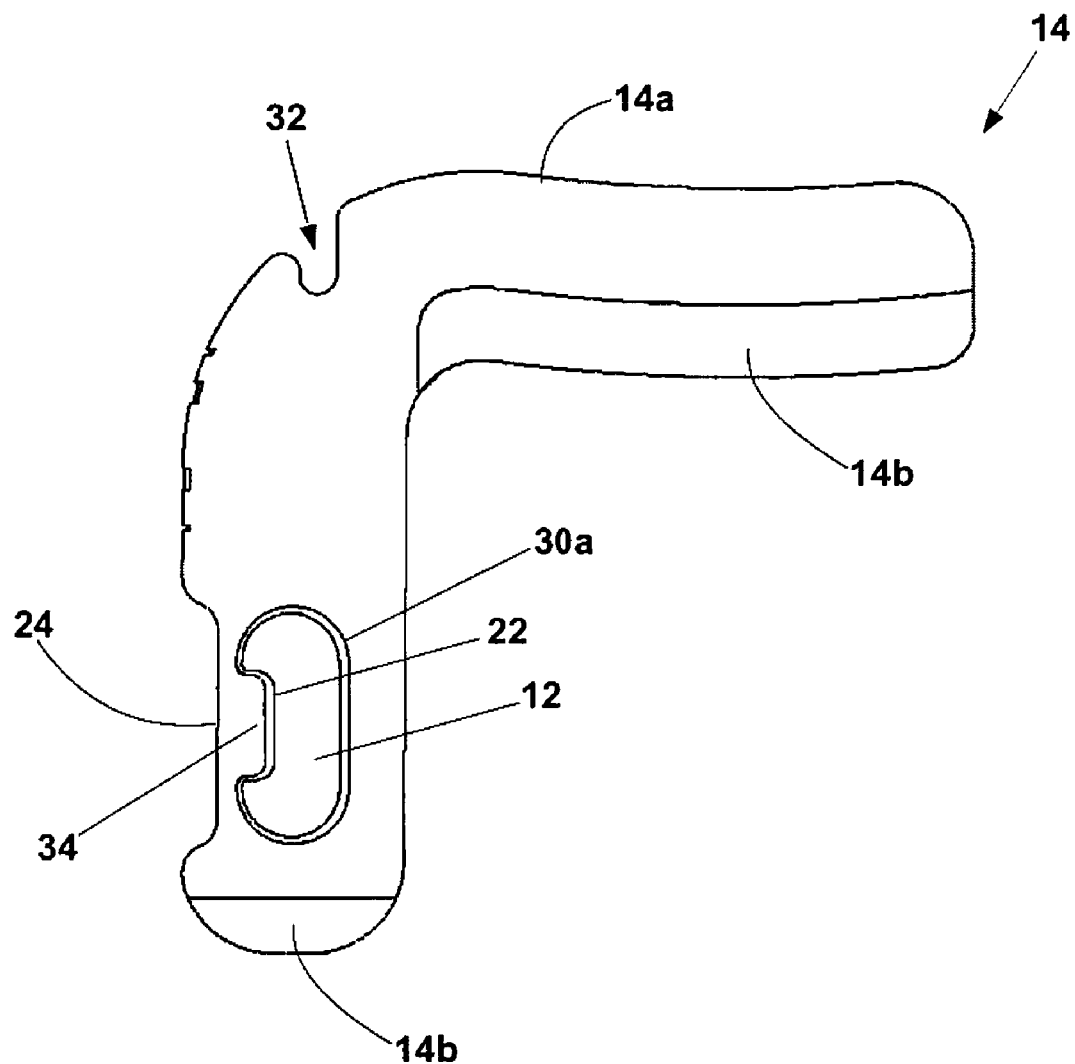
FIG. 14 depicts a cross-section view of a right side bite pad assembly of a low profile mouthguard according to a preferred embodiment of the invention.
Figure 15:
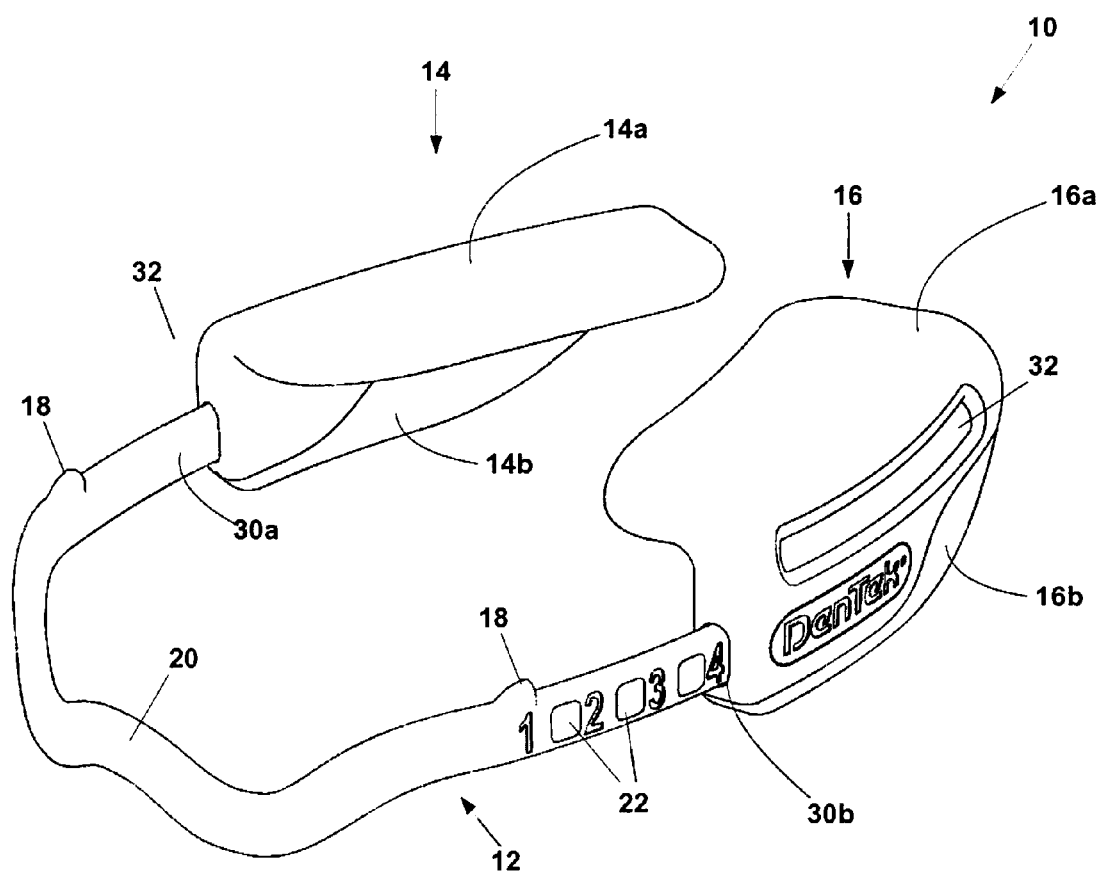
FIG. 15 depicts a front upper perspective view of a low profile mouthguard according to an alternative embodiment of the invention.
Figure 16:
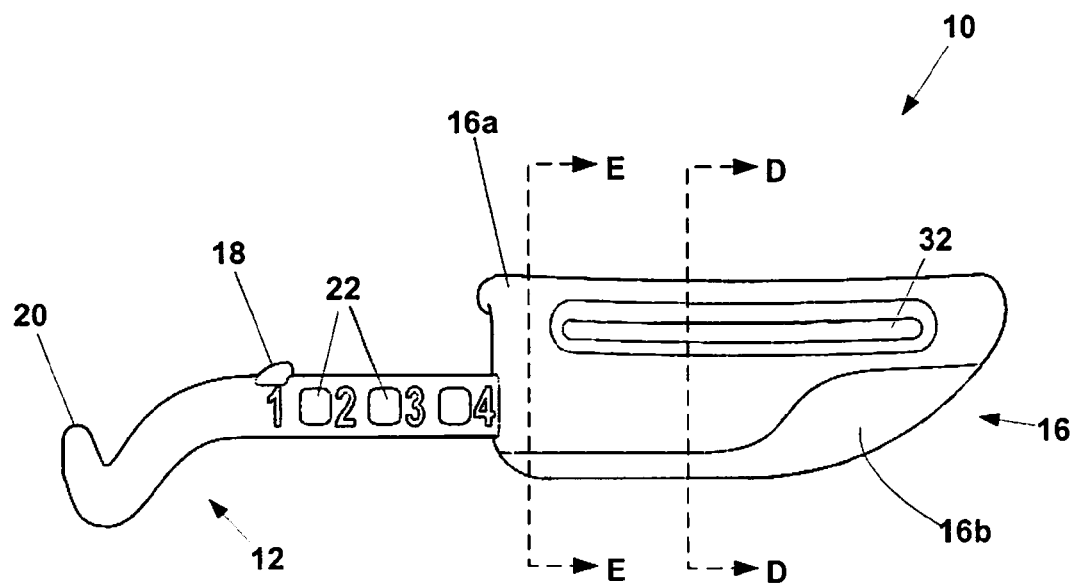
FIG. 16 depicts a left side elevation view of a low profile mouthguard according to an alternative embodiment of the invention.
Figure 17:
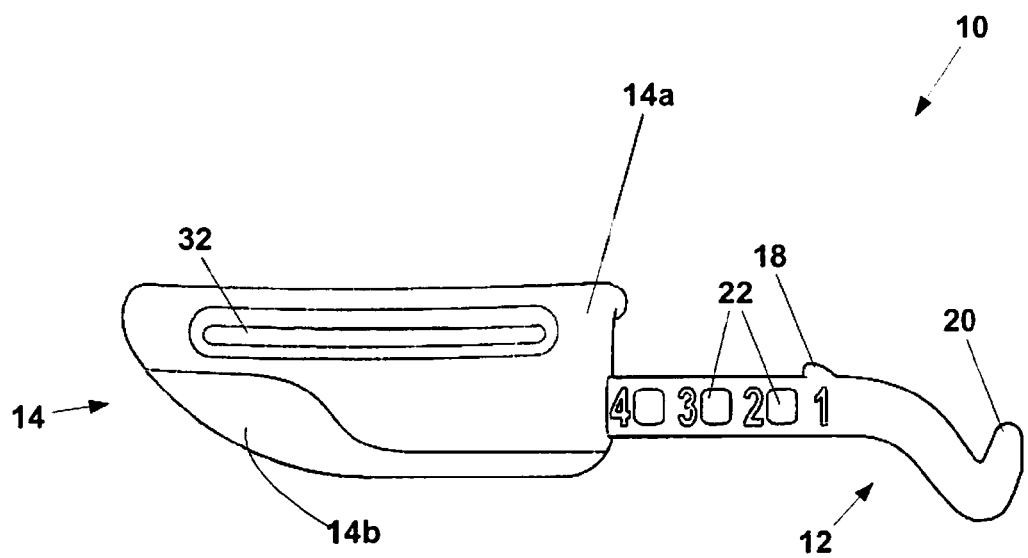
FIG. 17 depicts a right side elevation view of a low profile mouthguard according to an alternative embodiment of the invention.
Figure 18:
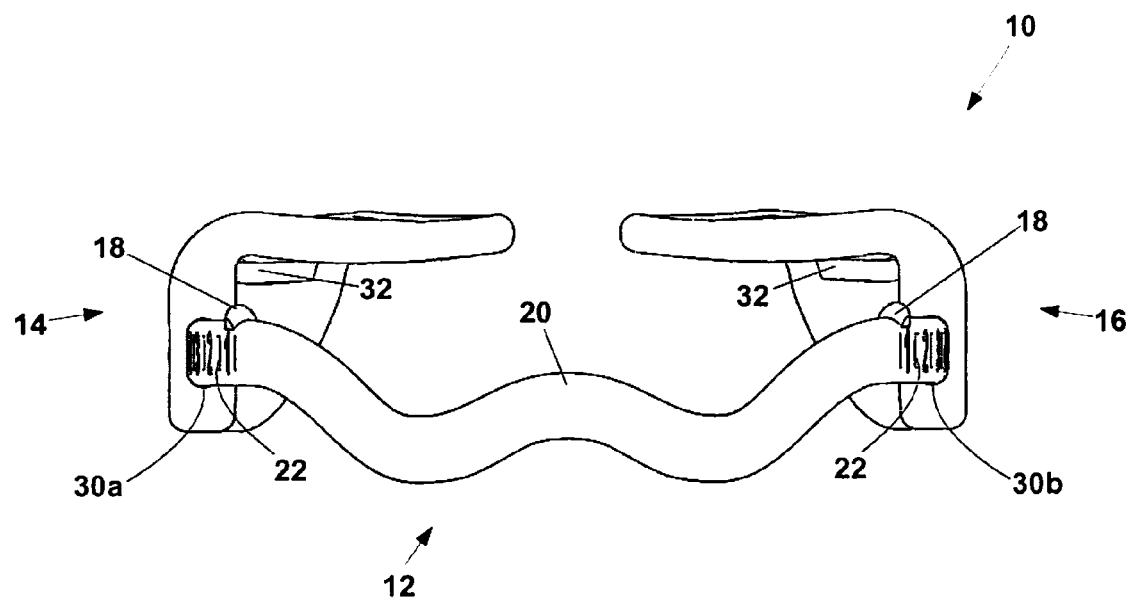
FIG. 18 depicts a front elevation view of a low profile mouthguard according to an alternative embodiment of the invention.
Figure 19:
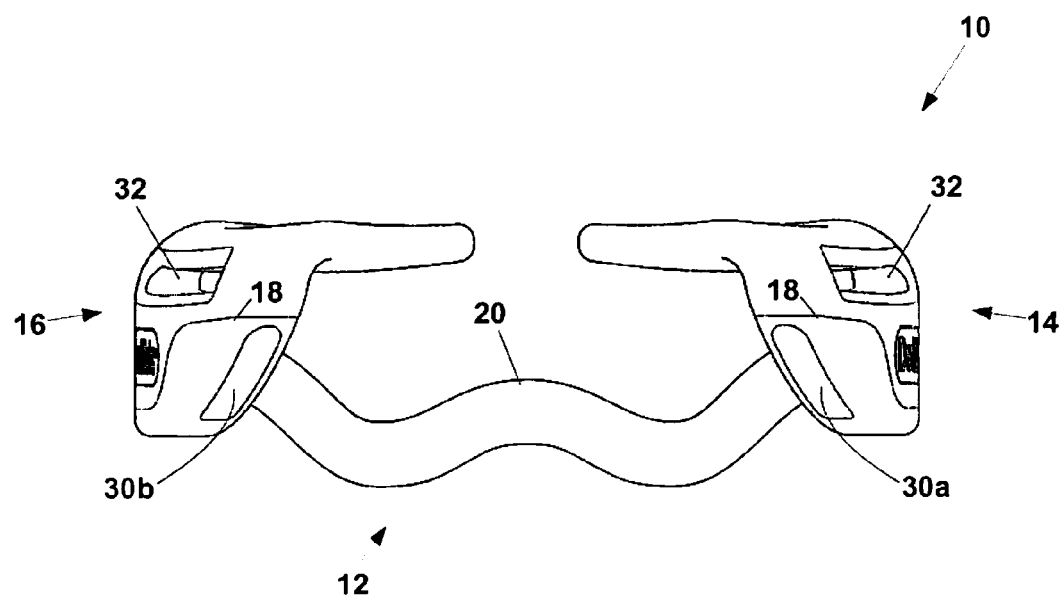
FIG. 19 depicts a rear elevation view of a low profile mouthguard according to an alternative embodiment of the invention.
Figure 20:
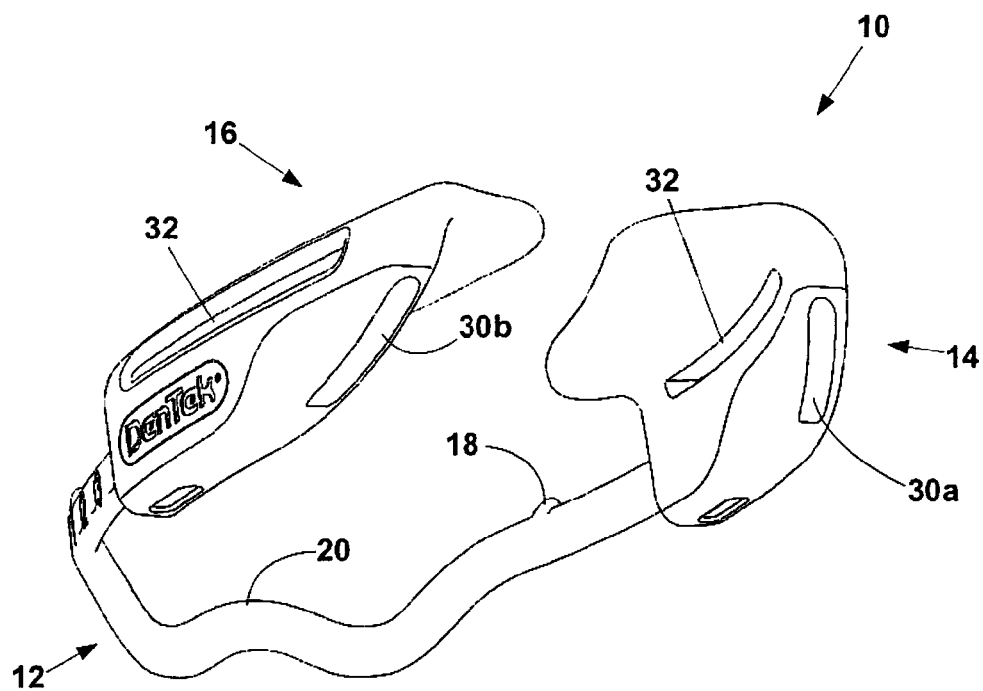
FIG. 20 depicts a rear lower perspective view of a low profile mouthguard according to an alternative embodiment of the invention.
Figure 21:
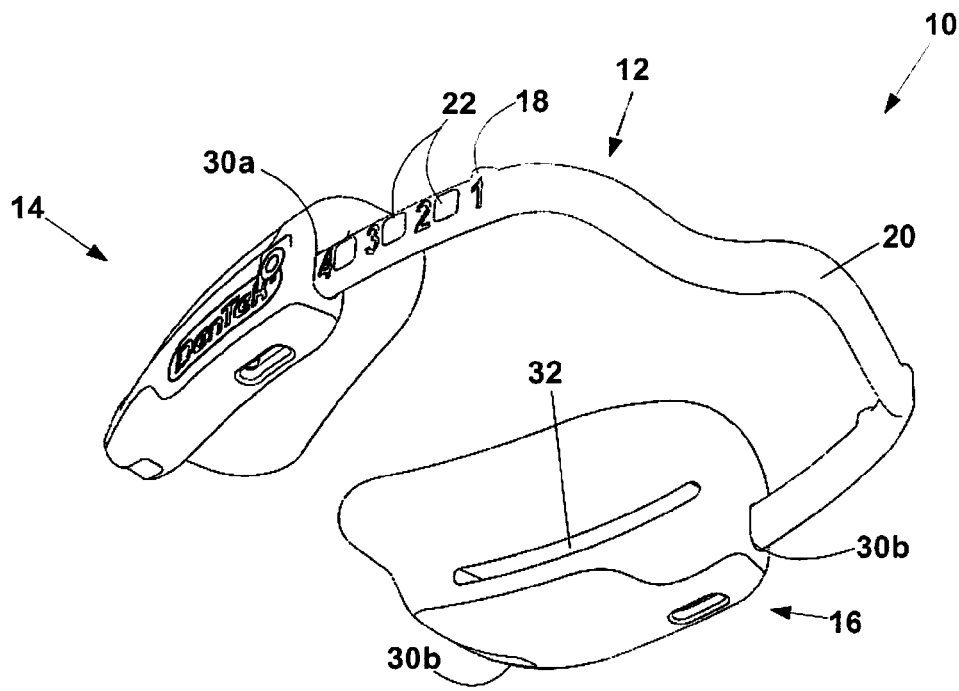
FIG. 21 depicts a front lower perspective view of a low profile mouthguard according to an alternative embodiment of the invention.
Figure 22:
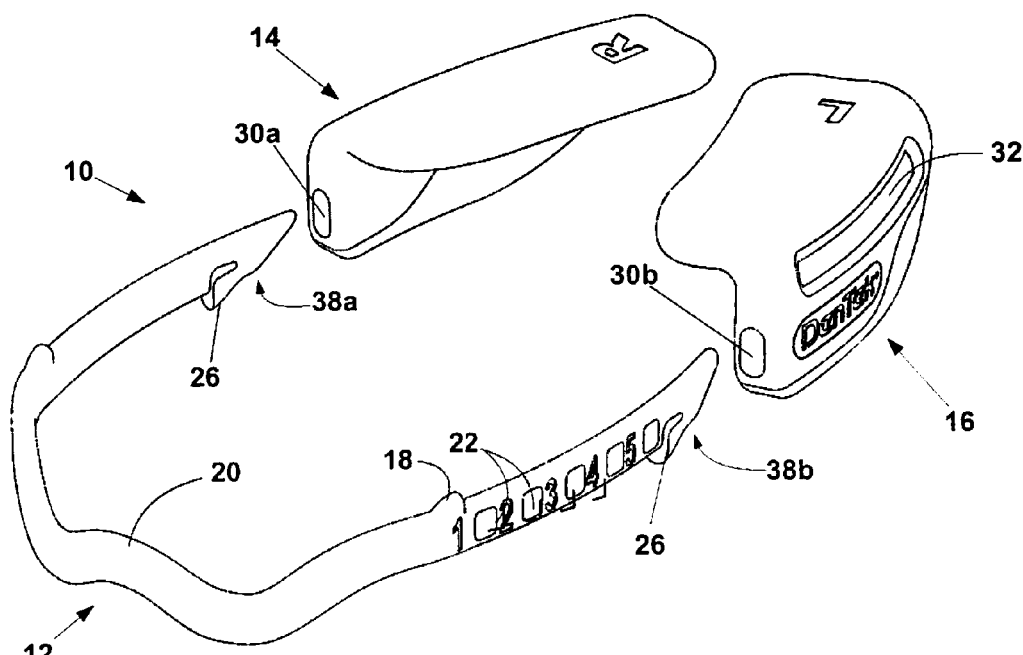
FIG. 22 depicts an exploded view of a low profile mouthguard according to an alternative embodiment of the invention.
Figure 23:
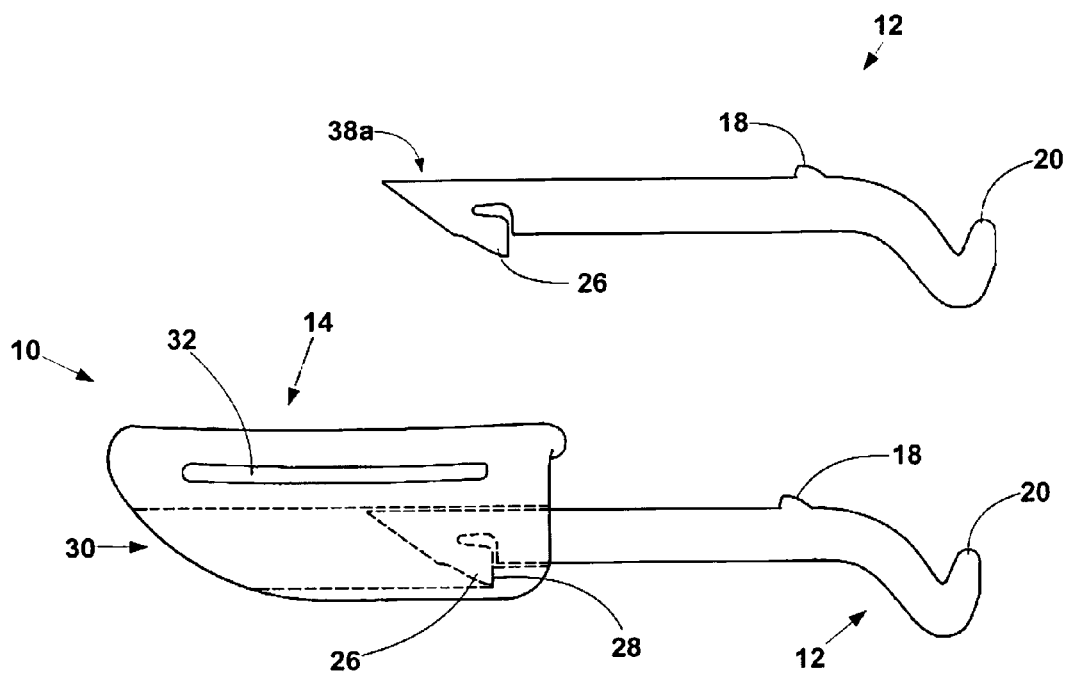
FIG. 23 depicts an internal view of a buccal strap retaining mechanism of a low profile mouthguard according to an alternative embodiment of the invention.
Figure 24:
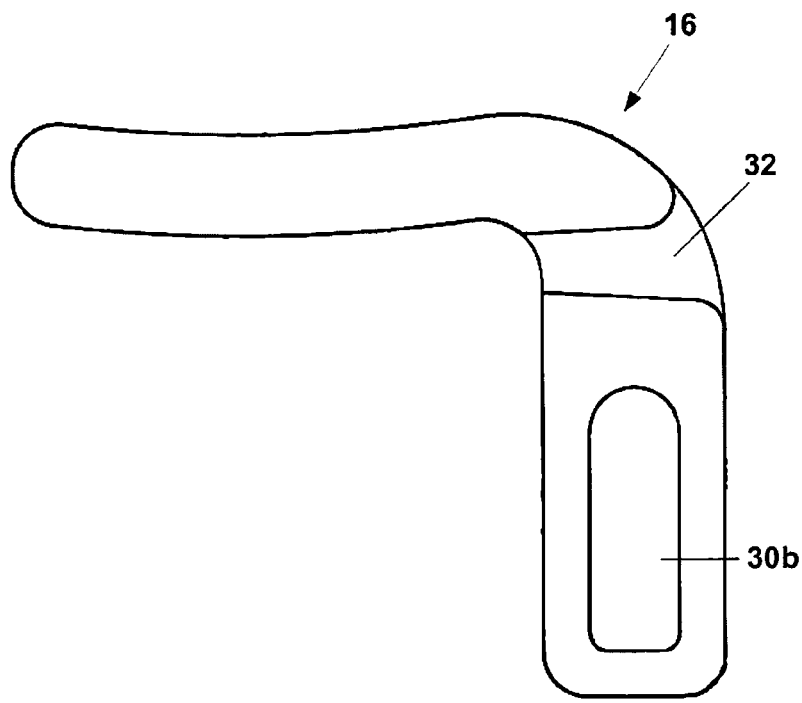
FIGS. 24 and 25 depict cross-section views of a left side bite pad assembly of a low profile mouthguard according to an alternative embodiment of the invention.
Figure 25:
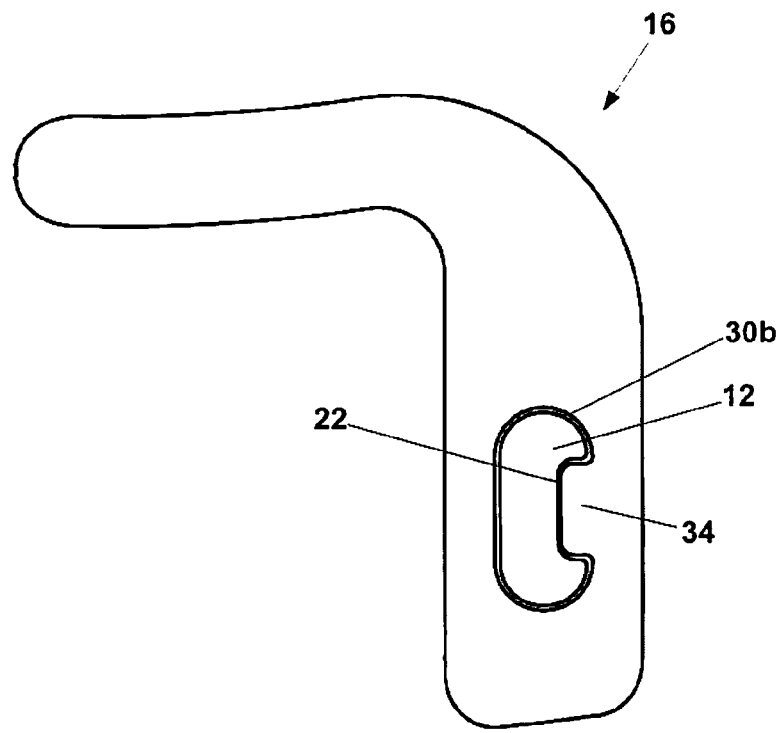

In a preferred embodiment, the forward-aft position of each bite pad assembly 14-16 may be independently adjusted by simply sliding the assemblies along the buccal strap 12. Four indentations 22 are provided along an outer surface of the buccal strap 12 to provide four adjustment positions. As shown in the cross-section view of FIG. 14, these indentations 22 are engaged by a protrusion 34 that extends inwardly from an inside wall of the channels 30a-30b. When the protrusion 34 engages an indentation 22, the bite pad assembly 14-16 is substantially secured at a corresponding one of the adjustment positions. In a preferred embodiment, a thin wall section 24 of the upper bite surface member 14a-14b can flex outward sufficiently to allow the protrusion 34 to engage or disengage an indentation 22 when sufficient forward or aft sliding force is applied.

Figure 11:
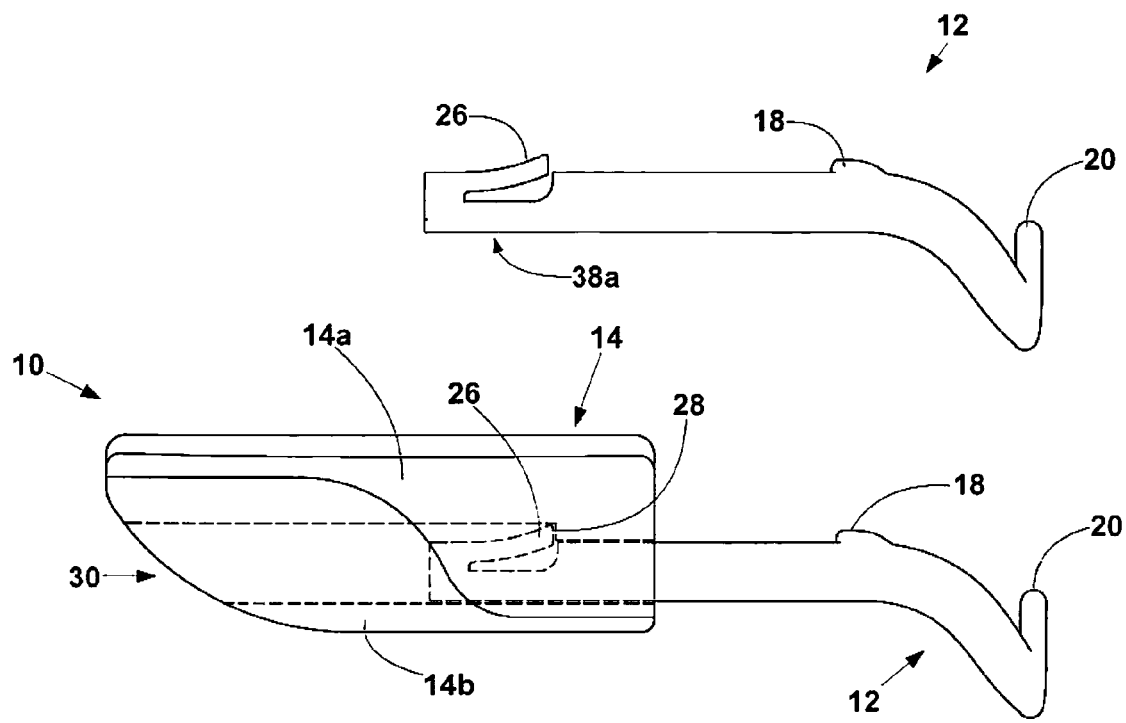
FIG. 11 depicts an internal view of a buccal strap retaining mechanism of a low profile mouthguard according to a preferred embodiment of the invention.

As shown in FIGS. 10 and 11, the aft end portions 38a-38b of the buccal strap 12 include upwardly protruding fingers 26 which engage downwardly extending lips 28 within portions of the channels 30a-30b that extend through the upper bite surface members 14a-16a. The engagement of the fingers 26 with the lips 28 prevents the bite pad assemblies 14-16 from being completely removed from buccal strap 12. During initial assembly of the mouthguard 10, the fingers 26 deflect sufficiently downward to allow the ends of the buccal straps 12 to be inserted into and slide through the forward portions of the channels 30a-30b. Thus, after initial assembly, the ends of the strap 12 are always contained within the bite pad assemblies.

As shown in the figures, the buccal strap 12 also includes raised shoulders 18 disposed forward of the indentations 22. The shoulders 18 provide a limit of forward travel for the bite pad assemblies 14-16.

In a preferred embodiment, each of the upper bite surface members 14a-16a includes a pair of tabs 36a that engage a corresponding pair of indentations 36b disposed on an inner edge of each of the lower bite surface members 14b-16b. The engagement of the tabs 36a with the indentations 36b aide in securing the upper bite surface members 14a-16a to the lower bite surface members 14b-16b and in preventing forward-aft slippage of the upper bite surface members 14a-16a with respect to the lower bite surface members 14b-16b.

In some embodiments of the invention, the occlusal bite surfaces of the upper bite surface members 14a-16a are curved to match the Curve of Spee. In other embodiments, the occlusal bite surfaces of the upper bite surface members 14a-16a are substantially flat.

As shown in the figures, preferred embodiments of the invention include troughs 32 molded into the buccal corners of the upper bite surface members 14a-16a. The troughs 32 allow flexing of the bite pad assemblies 14-16 to accommodate variations in the Curve of Wilson.

Figure 12:
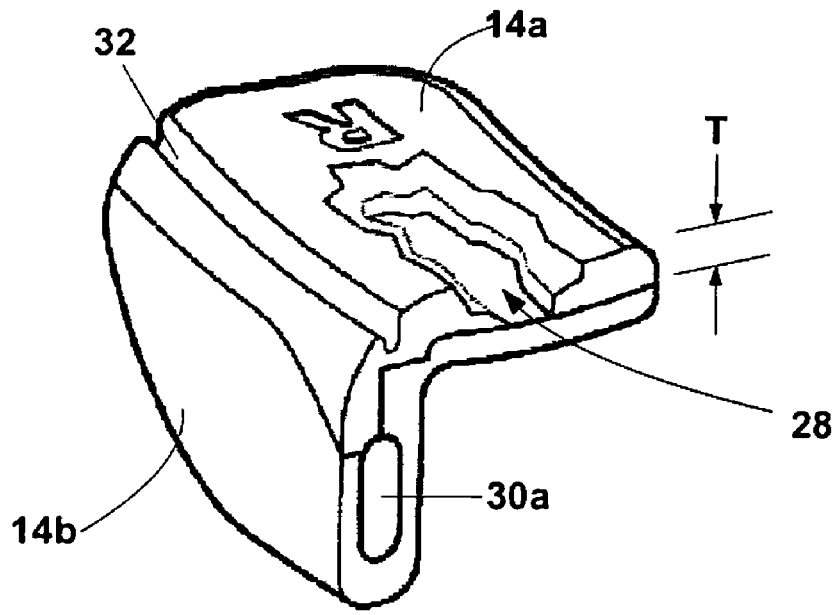
FIG. 12 depicts a cross-section view of a right side bite pad assembly of a low profile mouthguard according to a preferred embodiment of the invention.
Figure 13:
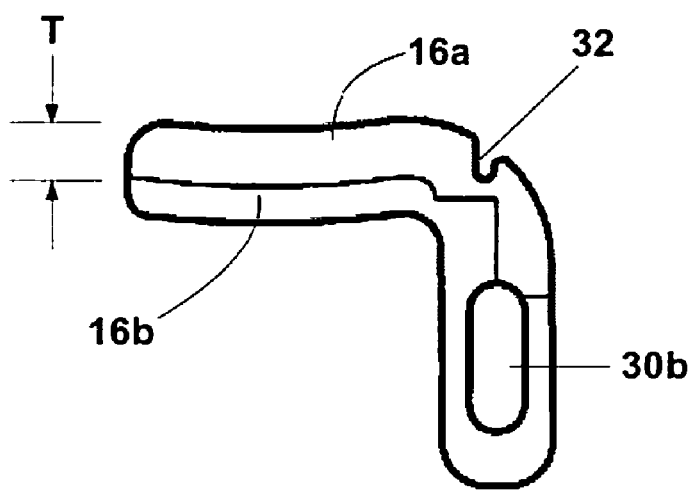
FIG. 13 depicts a cross-section view of a left side bite pad assembly of a low profile mouthguard according to a preferred embodiment of the invention.

As shown in FIGS. 12 and 13, the thickness T of the upper bite surface members 14a-16a is approximately 1.0 mm to 2.5 mm in a preferred embodiment. Preferably, the color of the material of the upper bite surface members 14a-16a is different from the color of the material of the lower bite surface members 14b-16b. Due to the difference in color, it becomes apparent when the material of the upper bite surface members 14a-16a has worn through to expose the material of the lower bite surface members 14b-16b as indicated at 28 in FIG. 12. This serves as a wear indicator to signal to the user that it is time to replace the mouthguard 10 with a new one. In one preferred embodiment, the upper bite surface members 14a-16a are white and the lower bite surface members 14b-16b are blue.

As shown in FIG. 1, the buccal strap 12 is downwardly curved along its frontal region. When the mouthguard 10 is inserted in the wearer's mouth, the downwardly curved frontal region of the buccal strap 12 is disposed within the vestibule region of the mouth between the lip and gum. In this position, the buccal strap 12 is generally out of the way of the wearer's tongue so that it does not interfere with speech. In the center of the buccal strap 12 is an upwardly arched portion 20 provided to accommodate the frenulum of the wearer's lower lip. This arched portion 20 further enhances the comfort of the mouthguard 10.

FIGS. 15-25 depict an alternative embodiment of the low-profile mouthguard 10. Although this embodiment is similar in many respects to the embodiment depicted in FIGS. 1-14, there are several differences, the most significant of which are listed below.

(1) The bite pad assemblies 14-16 comprise a monolithic molded structures (as opposed to the two-piece assemblies depicted in FIG. 10).
(2) The troughs 32 are in the form of elongate apertures that pass completely through the buccal corners of the bite pad assemblies 14-16. (See FIG. 24.)
(3) The curvature in the upwardly arched portion 20 of the buccal strap 12 is less pronounced.
(4) The fingers 26 within the channels 30a-30b the aft end portions 38a-38b of the buccal strap 12 are downwardly protruding to engage upwardly extending lips 28. (See FIG. 23.)

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A dental appliance comprising:
    a U-shaped buccal strap having opposing right and left aft end portions, the buccal strap including a plurality of indentations disposed adjacent the right and left aft portions;
    a right bite pad assembly slidingly connected to and completely enclosing the right aft end portion of the buccal strap, the right bite pad assembly comprising:
        a right upper bite surface member for contacting right upper molars of a wearer;
        a right lower bite surface member for contacting right lower molars of the wearer;
        a right channel extending through the right upper bite surface member and the right lower bite surface member, the right channel for receiving the right aft end portion of the buccal strap;
        a protrusion extending inwardly within the right channel, the protrusion for engaging one of the plurality of indentations in the right aft end portion of the buccal strap to provide for adjustment positioning; and
        a wall section that can flex outward sufficient to allow the protrusion to engage or disengage the indentations; and
    a left bite pad assembly slidingly connected to and completely enclosing the left aft end portion of the buccal strap, the left bite pad assembly comprising:
        a left upper bite surface member for contacting left upper molars of a wearer;
        a left lower bite surface member for contacting left lower molars of the wearer;
        a left channel extending through the left upper bite surface member and the left lower bite surface member, the left channel for receiving the left aft end portion of the buccal strap; and
        a protrusion extending inwardly within the left channel, the protrusion for engaging one of the plurality of indentations in the left aft end portion of the buccal strap to provide for adjustment positioning;
        a wall section that can flex outward sufficient to allow the protrusion to engage or disengage the indentations.

2. The dental appliance of claim 1 wherein the protrusion in the right bite pad assembly is disposed within a portion of the right channel that extends through the right upper bite surface member, and the protrusion in the left bite pad assembly is disposed within a portion of the left channel that extends through the left upper bite surface member.

3. The dental appliance of claim 1 wherein
    the right aft end portion of the buccal strap includes an upwardly extending finger which is operable to flex downward as the right aft end portion of the buccal strap is inserted into the right channel in the right bite pad assembly, the right channel of the right bite pad assembly includes a downwardly extending lip that is operable to engage the upwardly extending finger of the right aft end portion of the buccal strap to prevent complete withdrawal of the right aft end of the buccal strap from the right channel;
    the left aft end portion of the buccal strap includes an upwardly extending finger which is operable to flex downward as the left aft end portion of the buccal strap is inserted into the left channel in the left bite pad assembly, and the left channel of the left bite pad assembly includes a downwardly extending lip that is operable to engage the upwardly extending finger of the left aft end portion of the buccal strap to prevent complete withdrawal of the left aft end of the buccal strap from the left channel.

4. The dental appliance of claim 1 wherein the buccal strap includes a central arched portion for accommodating the frenulum of a wearer's lower lip.

5. The dental appliance of claim 1 further comprising a trough disposed in a buccal corner of each of the right and left upper bite surface members, wherein the trough is operable to allow flexing of the bite pad assemblies to accommodate variations in the Curve of Wilson.

6. The dental appliance of claim 1 wherein a forward portion of the right channel extends through the right upper bite surface member and a rear portion of the right channel extends through the right lower bite surface member, and a forward portion of the left channel extends through the left upper bite surface member and a rear portion of the left channel extends through the left lower bite surface member.

7. The dental appliance of claim 1 wherein the upper bite surface members are formed of a material having a color which is different from the color of the material of the lower bite surface members, such that when the material of the upper bite surface members wears through due to extended use of the appliance, the material of the lower bite surface members is exposed, thereby indicating that replacement of the appliance is desirable.

8. The dental appliance of claim 1 wherein the right bite pad assembly and the left bite pad assembly further comprise occlusal bite surfaces that are curved to match the curve of Spee.

9. A dental appliance comprising:
a U-shaped buccal strap having opposing right and left aft end portions;
a right bite pad assembly slidingly connected to and completely enclosing the right aft end portion of the buccal strap, the right bite pad assembly comprising:
  a right upper bite surface member for contacting right upper molars of a wearer;
  a right lower bite surface member for contacting right lower molars of the wearer; and
  a right channel extending into the right bite pad assembly for receiving the right aft end portion of the buccal strap and including a protrusion extending inwardly within the right channel; and
  a wall section that can flex outward sufficient to allow the protrusion to engage or disengage an indentation on the buccal strap; and
a left bite pad assembly slidingly connected to and completely enclosing the left aft end portion of the buccal strap, the left bite pad assembly comprising:
  a left upper bite surface member for contacting left upper molars of a wearer;
  a left lower bite surface member for contacting left lower molars of the wearer;
  a left channel extending into the left bite pad assembly for receiving the left aft end portion of the buccal strap and including a protrusion extending inwardly within the left channel; and
  a wall section that can flex outward sufficient to allow the protrusion to engage or disengage an indentation on the buccal strap,
  wherein the right aft end portion of the buccal strap includes an upwardly extending finger which is operable to flex downward as the right aft end portion of the buccal strap is inserted into the right channel in the right bite pad assembly,
  wherein the right channel of the right bite pad assembly includes a downwardly extending lip that is operable to engage the upwardly extending finger of the right aft end portion of the buccal strap to prevent complete withdrawal of the right aft end of the buccal strap from the right channel,
  wherein the left aft end portion of the buccal strap includes an upwardly extending finger which is operable to flex downward as the left aft end portion of the buccal strap is inserted into the left channel in the left bite pad assembly, and
  wherein the left channel of the left bite pad assembly includes a downwardly extending lip that is operable to engage the upwardly extending finger of the left aft end portion of the buccal strap to prevent complete withdrawal of the left aft end of the buccal strap from the left channel.

10. A dental appliance comprising:
a U-shaped buccal strap having opposing right and left aft end portions;
a right bite pad assembly slidingly connected to and completely enclosing the right aft end portion of the buccal strap, the right bite pad assembly including a right channel extending into the right bite pad assembly for receiving the right aft end portion of the buccal strap and a protrusion extending inwardly within the right channel; and
a wall section of the right bite pad assembly that can flex outward sufficient to allow the protrusion to engage or disengage an indentation on the buccal strap; and
a left bite pad assembly slidingly connected to and completely enclosing the left aft end portion of the buccal strap, the left bite pad assembly including a left channel extending into the left bite pad assembly for receiving the left aft end portion of the buccal strap and a protrusion extending inwardly within the left channel; and
a wall section of the left bite pad assembly that can flex outward sufficient to allow the protrusion to engage or disengage an indentation on the buccal strap
wherein the right aft end portion of the buccal strap includes a downwardly extending finger which is operable to flex upward as the right aft end portion of the buccal strap is inserted into the right channel in the right bite pad assembly,
wherein the right channel of the right bite pad assembly includes an upwardly extending lip that is operable to engage the downwardly extending finger of the right aft end portion of the buccal strap to prevent complete withdrawal of the right aft end of the buccal strap from the right channel,
wherein the left aft end portion of the buccal strap includes a downwardly extending finger which is operable to flex upward as the left aft end portion of the buccal strap is inserted into the left channel in the left bite pad assembly, and
wherein the left channel of the left bite pad assembly includes an upwardly extending lip that is operable to engage the downwardly extending finger of the left aft end portion of the buccal strap to prevent complete withdrawal of the left aft end of the buccal strap from the left channel.

11. A dental appliance comprising:
a U-shaped buccal strap having opposing right and left aft end portions and including a plurality of indentations disposed adjacent the right and left aft end portions;

a right bite pad assembly slidingly connected to and completely enclosing the right aft end portion of the buccal strap, the right bite pad assembly comprising:
- a right upper bite surface member for contacting right upper molars of a wearer;
- a right lower bite surface member for contacting right lower molars of the wearer;
- a right channel extending into the right bite pad assembly for receiving the right aft end portion of the buccal strap;
- a protrusion extending inwardly within the right channel, the protrusion for engaging one of the plurality of indentations in the right aft end portion of the buccal strap to provide for adjustment positioning; and
- a wall section that can flex outward sufficient to allow the protrusion to engage or disengage the indentations; and a left bite pad assembly slidingly connected to and completely enclosing the left aft end portion of the buccal strap, the left bite pad assembly comprising:
- a left upper bite surface member for contacting left upper molars of a wearer;
- a left lower bite surface member for contacting left lower molars of the wearer;
- a left channel extending into the left bite pad assembly for receiving the left aft end portion of the buccal strap;
- a protrusion extending inwardly within the left channel, the protrusion for engaging one of the plurality of indentations in the left aft end portion of the buccal strap to provide for adjustment positioning; and
- a wall section that can flex outward sufficient to allow the protrusion to engage or disengage the indentations.

12. A dental appliance comprising:

a U-shaped buccal strap having opposing right and left aft end portions, and a plurality of indentations disposed adjacent the right and left aft end portions;

a right bite pad assembly slidingly connected to and completely enclosing the right aft end portion of the buccal strap, the right bite pad assembly including:
- a right channel extending through the right bite pad assembly, the right channel for receiving the right aft end portion of the buccal strap; and
- a protrusion extending inwardly within the right channel, the protrusion for engaging one of the plurality of indentations in the right aft end portion of the buccal strap to provide for adjustment positioning; and
- a wall section that can flex outward sufficient to allow the protrusion to engage or disengage the indentations; and a left bite pad assembly slidingly connected to and completely enclosing the left aft end portion of the buccal strap, the left bite pad assembly including:
- a left channel extending through the left bite pad assembly, the left channel for receiving the left aft end portion of the buccal strap; and
- a protrusion extending inwardly within the left channel, the protrusion for engaging one of the plurality of indentations in the left aft end portion of the buccal strap to provide for adjustment positioning; and
- a wall section that can flex outward sufficient to allow the protrusion to engage or disengage the indentations.

\* \* \* \* \*